US006838548B1

(12) United States Patent
Tsuganezawa

(10) Patent No.: US 6,838,548 B1
(45) Date of Patent: Jan. 4, 2005

(54) ARTIODACTYL EPIMORPHINE

(75) Inventor: Keiko Tsuganezawa, Kanagawa (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 09/744,989

(22) PCT Filed: Aug. 20, 1999

(86) PCT No.: PCT/JP99/04479

§ 371 (c)(1),
(2), (4) Date: Aug. 24, 2001

(87) PCT Pub. No.: WO00/11146

PCT Pub. Date: Mar. 2, 2000

(30) Foreign Application Priority Data

Aug. 20, 1998 (JP) .......................................... 10/233892

(51) Int. Cl.$^{7}$ ......................... C07K 14/75; C07H 21/04
(52) U.S. Cl. ...................................... 530/350; 536/23.5
(58) Field of Search ........................ 536/23.5; 530/350; 514/12

(56) References Cited

U.S. PATENT DOCUMENTS

| | | | |
|---|---|---|---|
| 5,726,298 | A | 3/1998 | Hirai et al. |
| 5,837,239 | A | 11/1998 | Hirai et al. |
| 6,127,149 | A | 10/2000 | Hirai et al. |

FOREIGN PATENT DOCUMENTS

| | | |
|---|---|---|
| CA | 2152210 | 12/1995 |
| JP | 6-25295 | 2/1994 |
| JP | 6293800 | 10/1994 |
| JP | 8-325293 | 12/1996 |
| JP | 9-65885 | 3/1997 |
| WO | 98/22505 | 5/1998 |

OTHER PUBLICATIONS

An English Language abstract of JP 6–293800.

Oka et al., "Inductive influences of epimorphin on endothelial cells in vitro", Exp. Cell Res., vol. 222, No. 1, Oct. 1, 1996, pp. 189–198.

Patent Abstracts of Japan for JP 9–65885.

Oka et al., "Inductive Influences of Epimorphin on Endothelial Cells in Vitro", *Experimental Cell Research,* 222, pp. 189–198 (1996).

Hirai et al., "Epimorphin: A Mesenchymal Protein Essential for Epithelial Morphogenesis", *Cell,* vol. 69, pp. 471–481 (1992).

Gumbiner, "Epithelial Morphogenesis", *Cell,* vol. 69, pp. 385–387 (1992).

Zha et al., "The Epimorphin Gene is Highly Conserved among Humans, Mice, and Rats and Maps to Human Chromosome 7, Mouse Chromosome 5, and Rat Chromosome 12", *Genomics,* 37, pp. 386–389 (1996).

Hirai, "Molecular Cloning of Human Epimorphin: Identification of Isoforms and Their Unique Properties", *Biochemical Biophysical Research Communications,* vol. 191, No. 3, pp. 1332–1337 (1993).

Oka et al., SDB Meeting Abstract (B216) of 13th International Congress of Developmental Biology 56th SDB Annual Meeting, *Developmental Biology* vol. 186 (1997).

Koshida et al., "Identification of Cellular Recognition Sequence of Epimorphin and Critical Role of Cell/Epimorphin Interaction in Lung Branching Morphogenesis", *Biochemical and Biophysical Research Communications,* vol. 234, No. 2, pp. 522–525 (1997).

Hirai et al., "Epimorphin Functions as a Key Morphoregulator for Mammary Epithelial Cells", *The Journal of Cell Biology,* vol. 140, pp. 159–169 (1998).

Panaretto, "Gene Expression of Potential Morphogens during Hair Follicle and Tooth Formation: a Review", *Reprod. Fertil. Dev.,* pp. 345–360 (1993).

Matsuki et al., "Gene Expression of Epimorphin in Rat Incisor Ameloblasts", *Archs Oral Biol.,* vol. 40, No. 2, pp. 161–164 (1995).

*Primary Examiner*—David Romeo
(74) *Attorney, Agent, or Firm*—Greenblum & Bernstein, P.L.C.

(57) ABSTRACT

An epimorphin protein having action to induce differentiation of milk protein-producing cells into a branched luminal structure in Artiodactyls including cows and sheep and comprising an amino acid sequence set forth in SEQ ID NO: 1 in the Sequence Listing; and a gene encoding said protein are provided. The epimorphin protein of the present invention can be used as a medicament for Artiodactyls or an agent for modifying animal properties. For example, the protein acts to enlarge the mammary gland of cows or sheep to prevent the gland from clogging, thereby a yield of a desired protein secreted in the milk of the animal is increased.

11 Claims, No Drawings

ARTIODACTYL EPIMORPHINE

TECHNICAL FIELD

The present invention relates to epimorphin derived from the order Artiodactyla including pigs, cows, sheep and the like.

BACKGROUND ART

Morphology of various organs of animals is constructed by epithelial tissues, and mesenchymal cells exist around the tissues. An epimorphin is a cell membrane protein that is expressed in mesenchymal cells, particularly in a high amount neighboring epithelial cells (Hirai, Y., et al., Cell, 69, pp. 471–481, 1992). It is considered that the progress of morphogenesis of the epithelial tissue requires a signal from the mesenchymal cells (Gumbiner, B. M., Cell., 69, pp. 385–387, 1992). Epimorphins have been cloned in humans, birds, and rats as well as in mice. The presences of isoforms are known which have a different sequence of a hydrophobic site (Zha, H., et al., Genomics, 37, pp. 386–389, 1996; Hirai, Y., et al., Biochem. Biophys. Res. Commun., 191, p. 1332–1337, 1993; Oka, Y., Developmental Biological Society, 1997, May).

Epimorphin is known to be deeply involved in morphogenesis by epithelial tissues in mice, i.e., differentiation into hair on the fetal talon skin, and differentiation into luminal structure in the fetal lung (Hirai, Y., et al., Cell, 69, pp. 471–481, 1992; Koshida, S., et al., Biochem. Biphys. Res. Commun., 234, pp. 522–526, 1997). Moreover, epimorphin activates mesenchymal cells and promotes secretion of cytokines, IL-6 and IL-8 (Oka, Y., et al., Exp. Cell Res., 222, pp. 189–198, 1996). Recently, it was revealed that the addition of epimorphin to milk protein-producing SCp2 cells induces cell growth to form a branched duct structure (Hirai, Y., et al., J. cell Biol., 140, pp. 159–169, 1998). Epimorphin is expected to be effective in elucidating the mechanism of onset of diseases due to abnormality of organs, developing methods for diagnosing and treating said diseases, generating hairs, lumens, bones, and teeth, generating new blood vessels, and developing new methods for treatment of injuries (Zha, H., et al., Genomics, 37, pp. 386–389, 1996; Panaretto, B. A., Reprod. Fertil. Dev., 5, pp. 345–360, 1993; Matsuki, Y., et al, Archs. Oral Biol., 40, pp. 161–164, 1995).

DISCLOSURE OF THE INVENTION

A so-called animal factory, which allows an animal to secrete a desired protein in its milk, has recently been used practically. Mammals of the order Artiodactyla including cows and sheep are often utilized as animals for the secretion of a desired protein in milk. However, particularly when a desired protein has a relatively large molecular weight or when the secretion amount of a desired protein becomes high, mammary glands may often clog and the desired protein cannot be extracorporeally recovered. Accordingly, for practical application of an effective animal factory, it is required that means be developed which enlarges the mammary glands of such animals and prevents the mammary glands of the animals from clogging even when a large amount of the desired protein is produced in the milk.

The inventors of the present invention have focused on the fact that epimorphin induces differentiation of SCp2 cells into a branched duct structure, and conducted various studies to isolate an epimorphin gene of Artiodactyls. As a result, the inventors have succeeded in the isolation of an epimorphin gene derived from an animal belonging to Artiodactyls, and found that the gene product has an activity of enlarging mammary glands, i.e., an activity of differentiating mammary cells so as to enlarge the internal diameters of the ducts. The present invention was achieved on the basis of these findings.

The present invention thus provides a protein comprising an amino acid sequence set forth in SEQ ID NO: 1 in the Sequence Listing (also referred to as "bovine epimorphin 2"), a protein comprising an amino acid sequence set forth in SEQ ID NO: 3 in the Sequence Listing (also referred to as "bovine epimorphin 4"), and a protein comprising an amino acid sequence set forth in SEQ ID NO:5 in the Sequence Listing (also referred to as "sheep epimorphin 2"). The present invention also provides a protein having 95% or more homology to an amino acid sequence from the 1st to 262nd amino acids set forth in SEQ ID NO: 1 (bovine epimorphin 2) in the Sequence Listing; a protein having an amino acid sequence from the 1st to 262nd amino acids set forth in SEQ ID NO: 1 in the Sequence Listing; and a protein having an amino acid sequence from the 1st to 262nd amino acids set forth in SEQ ID NO: 5 in the Sequence Listing.

The invention further provides a protein having any one of the amino acid sequences set forth in SEQ ID NOS: 1, 3, and 5 in the Sequence Listing wherein one or more amino acids are substituted, deleted, and/or added, and inducing differentiation of milk protein-producing cells derived from mammals, preferably those derived from Artiodactyla, into a branched luminal structure; and a protein having any one of the amino acid sequences of SEQ ID NOS: 1, 3, and 5 in the Sequence Listing wherein one or more amino acids are substituted, deleted, and/or added, and promoting hair growth in mammals, preferably in Artiodactyls.

Furthermore, the present invention provides a protein in which one or more amino acids are substituted, deleted, and/or added in an amino acid sequence defined by the 1st to 262nd amino acids of either of the amino acid sequence set forth in SEQ ID NOS: 1 or 5 in the Sequence Listing, which has 95% or more homology to the amino acid sequence defined by the 1st to 262nd amino acids of either of the amino acid sequence set forth in SEQ ID NO: 1 or 5 and induces differentiation of milk protein-producing cells into a branched luminal structure; and a protein in which one or more amino acids are substituted, deleted, and/or added in an amino acid sequence defined by the 1st to 262nd amino acids of either of the amino acid sequence set forth in SEQ ID NOS: 1 or 5 in the Sequence Listing, which has 95% or more homology to the amino acid sequence defined by the 1st to 262nd amino acids of either of the amino acid sequence set forth in SEQ ID NO: 1 or 5 and promotes hair growth.

From another aspect, the present invention provides a polynucleotide encoding each of the above-mentioned proteins. According to preferred embodiments of the invention, DNAs set forth in SEQ ID NOS: 2, 4, and 6 are provided. The invention also provides a DNA comprising continuous 12 or more nucleotides contained in said nucleotide sequences in the Sequence Listing. The DNA may be either double- or single-strand, and may be either a sense or antisense strand when the DNA is single-stranded. Furthermore, the invention provides RNA hybridizing to the above DNA, and a polynucleotide as being the above polynucleotide with chemical modification.

The present invention also provides a recombinant vector having the aforementioned polynucleotide, a transformant such as a microbial cell and a mammalian cell which comprises said vector, and a process of producing the above proteins which comprises the steps of isolating and purifying the protein from a culture obtained by cultivation of said transformant. The present invention further provides an antibody, preferably a monoclonal antibody, recognizing each of the above proteins.

BEST MODE FOR CARRYING OUT THE INVENTION

Three isoforms of epimorphins are known to exist (Hirai Y., et al., J. Cell Biol., 140, pp. 159–169, 1998). These isoforms are classified as isoforms 1, 2 and 3, based on the number of amino acids at the C-terminal portion and their properties (hydrophobicity or hydrophilicity). According to this classification, bovine epimorphin 2 comprising an amino acid sequence set forth in SEQ ID NO: 1 in the Sequence Listing, and sheep epimorphin 2 comprising an amino acid sequence set forth in SEQ ID NO: 5 in the Sequence Listing, which are preferable examples of the present invention, are both classified as isoform 2. Bovine epimorphin 4 comprising an amino acid sequence set forth in SEQ ID NO: 3 in the Sequence Listing fails to comply with any one of the above classifications and is recognized as a new type of isoform.

Structurally, epimorphins can be divided into four domains. Also in the specification, epimorphins of the present invention are structurally divided into four portions, each referred to as domain 1, domain 2, domain 3, and domain 4 in the order from the N-terminal side. Domains 1 to 4 of the above-mentioned bovine epimorphin 2, bovine epimorphin 4, and sheep epimorphin 2 are as follows (an amino acid sequence set forth in SEQ ID NO:1 in the Sequence Listing will be simply referred to as "Amino acid sequence 1," which will apply to all the other sequences).

Bovine epimorphin 2

Domain 1: 1st to 107th amino acids of amino acid sequence 1

Domain 2: 108th to 187th amino acids of amino acid sequence 1

Domain 3: 188th to 262nd amino acids of amino acid sequence 1

Domain 4: 263rd to 287th amino acids of amino acid sequence 1

Bovine epimorphin 4

Domain 1: 1st to 107th amino acids of amino acid sequence 3

Domain 2: 108th to 187th amino acids of amino acid sequence 3

Domain 3: 188th to 262nd amino acids of amino acid sequence 3

Domain 4: 263rd to 269th amino acids of amino acid sequence 3

Sheep epimorphin 2

Domain 1: 1st to 107th amino acids of amino acid sequence 5

Domain 2: 108th to 187th amino acids of amino acid sequence 5

Domain 3: 188th to 262nd amino acids of amino acid sequence 5

Domain 4: 263rd to 287th amino acids of amino acid sequence 5

Domains 1 and 3 are coiled coil regions referred to as "a coiled coil region on the N side" and "a coiled coil region on the C side", respectively. Domain 4 is a hydrophobic domain referred to as the C-terminal hydrophobic region. Each of these domains is known to have the following functions, based on the findings about human and mouse epimorphin.

Domain 1: Promotion of differentiation into hair on the fetal talon skin, differentiation into luminal structure in the fetal lung, activation of mesenchymal cells, and promotion of secretion of cytokines, IL-6 and IL-8.

Domain 2: Cell adhesion and promotion of secretion of GM-CSF (a growth factor, a type of cytokine Domain 3: Function unknown Domain 4: Type 1 cell membrane binding domain Functions of Domains 1 and 2 are engaged in promotion of differentiation of milk protein-producing cells into luminal structure. Functions of epimorphins and their domains can be determined by methods described in publications. The present invention further encompasses polypeptides corresponding to each of the domains explained as for bovine epimorphin 2, bovine epimorphin 4, and sheep epimorphin 2; and a polypeptide having one of the amino acid sequences of each of these domains, in which one or more amino acids are substituted, deleted, and/or added, and having a biological action substantially the same as that of each of the domains.

As for the above three types of epimorphin, the amino acid sequence from the 1st to 262nd amino acids of the bovine epimorphin 2 is completely identical to that from the 1st to 262nd amino acids of bovine epimorphin 4. Furthermore, this sequence has 99.2% homology to the sequence from the 1st to 262nd amino acids of sheep epimorphin 2 and the sequences are well conserved. Therefore, the region of the amino acid sequences is a characteristic amino acid sequence for Artiodactyla epimorphin, and a protein comprising said amino acid sequence is a preferred embodiment of the present invention. Any proteins having homology of 95% or more, preferably 98% or more, with the amino acid sequence from the 1st to 262nd amino acids of the bovine epimorphin 2, and having a function substantially equivalent to that of the above amino acid sequence fall within the scope of the present invention. In addition, sheep epimorphin 2 and human epimorphin have 94.3% homology in an amino acid sequence from the 1st to 262nd amino acids, which are also well conserved. The term "homology" herein used means the maximum value obtained by subjecting one amino acid sequence to alignment based on the other sequence where the two sequences are compared. Such alignment can be conducted conveniently by using a commercially available computer software. An example of the software includes Genetics-Mac sold by Software Developing Co., Ltd.

The present invention also encompasses within the scope a protein having any one of the amino acid sequences set forth in SEQ ID NOS: 1, 3, and 5 in the Sequence Listing, in which one or more amino acids are substituted, deleted and/or added, and inducing differentiation of milk protein-producing cells into branched luminal structure; and a protein having any one of the amino acid sequences set forth in SEQ ID NOS: 1, 3, and 5 in the Sequence Listing, in which one or more amino acids are substituted, deleted and/or added, and promoting hair growth (these proteins are herein also referred to as "modified proteins" and where "protein(s) of the present invention" is referred to, the description is used to also encompass these modified proteins unless otherwise specifically mentioned). The action of inducing differentiation of milk protein-producing cells into branched luminal structure can be determined by methods described in J. Cell Biol., 140, pp. 159–169, 1998. It is also recognized that known epimorphins have hair growth promoting action (Hirai, Y., et al., Cell, 69, pp. 471–481, 1992).

These modified proteins can be produced by treating *Escherichia coli* having a DNA encoding any one of the amino acid sequences set forth in SEQ ID NOS: 1, 3 and 5 with an agent such as N-nitro-N-nitro-N-nitrosoguanidine to cause mutation, recovering a gene encoding a modified protein from the bacterial cells; and performing an ordinary gene expression. In addition, the gene may be directly treated with an agent such as sodium sulfate, or nucleotide deletions, substitutions or additions may be directly introduced into the gene by techniques such as site-specific mutation method (Kramer, W. et al., Methods in Enzymology, 154, 350, 1987) and recombinant PCR method (PCR Technology, Stockton press, 1989).

Methods to obtain genes encoding the protein of the present invention are not particularly limited. For example, a genetic DNA can be efficiently recovered by methods specifically described in the examples of the specification. It is well known to persons skilled in the art that, due to degeneracy of genetic codes, at least a part of nucleotides of the nucleotide sequence of the polynucleotide can be replaced with other types of nucleotides without changing the amino acid sequence of the polypeptide produced based on the polynucleotide. Therefore, the polynucleotides of the present invention encompass any epimorphin genes encoding any one of the amino acid sequences set forth in SEQ ID NOS: 1, 3, and 5. As preferable examples of the genes of the present invention, DNAs encoding bovine epimorphin 2, bovine epimorphin 4, and sheep epimorphin 2 are shown in SEQ ID NOS: 1, 4, and 6, respectively.

Antisense polynucleotides and derivatives thereof also fall within the scope of the present invention, which have a nucleotide sequence of an antisense strand of the polynucleotide encoding the protein of the present invention. Although the antisense polynucleotides are provided as a class of an embodiment of the aforementioned polynucleotides, the polynucleotides may also be herein referred to as "antisense polynucleotides" to specify that they are polynucleotides particularly having a nucleotide sequence of an antisense strand. The antisense polynucleotide can hybridize to a polynucleotide encoding each of the above proteins, and where a polynucleotide to which the antisense polynucleotide hybridizes is a polynucleotide in a coding region, biosynthesis of a polypeptide encoded by said polynucleotide can be inhibited.

An antisense polynucleotide for inhibiting the biosynthesis of the polypeptide preferably comprises 12 or more nucleotides, further preferably comprises 16 or more nucleotides. An unnecessarily long sequence is not preferred to achieve incorporation of the full length of an antisense polynucleotide into cells. For intracellular incorporation of the antisense polynucleotide to induce inhibition of the biosynthesis of the above proteins, the antisense polynucleotides comprising 12 to 30 nucleotides, preferably 15 to 25 nucleotides, more preferably 18 to 22 nucleotides may preferably be used.

The antisense polynucleotides or derivatives thereof of the present invention encompass any of those comprising multiply bound nucleotides each consisting of a base, a phosphoric acid, and a sugar, regardless of they are naturally or non-naturally derived. Typical examples include a natural antisense DNA and antisense RNA. Examples of non-natural polynucleotides include methylphosphonate-type and phosphorothioate type polynucleotides. Various antisense polynucleotide derivatives having excellent abilities of binding to a target DNA or mRNA, tissue specificity, cell-permeability, nuclease resistance, and intracellular stability can be obtained by applying methods in antisense technology available to persons skilled in the art.

Generally, from a viewpoint of easy hybridization, it is preferable to design antisense polynucleotides and derivatives thereof having a nucleotide sequence complementary to that in a region forming an RNA loop. In addition, an antisense polynucleotide that has a sequence complementary to a sequence of around a translation initiating codon, a ribosome binding site, a capping site, or a splicing site can be expected to have a high suppressing effect on expression. Among the antisense polynucleotides and derivatives thereof, those comprising a sequence complementary to genes encoding each of the above proteins, or to a sequence of around a translation initiation codon by mRNA, a ribosome binding site, a capping site, and/or a splicing site are preferred from a viewpoint of the effect on the suppression of expression.

Among polynucleotide derivatives widely known to date, an example of the derivatives having at least one enhanced abilities of nuclease resistance, tissue specificity, cell-permeability, and binding ability includes a derivative having phosphorothioate bondings as a backbone structure. The polynucleotides and derivatives thereof of the present invention encompass the aforementioned derivatives having these functions or said structure.

Among the antisense polynucleotides of the present invention, natural antisense polynucleotides can be prepared by using a chemical synthesizer, or by carrying out the PCR using a DNA encoding each of the above proteins as a template. The methyl phosphonate-type or phoshorothioate-type polynucleotide derivatives can generally be produced by chemical synthesis. For the synthesis, operations may be conducted according to an instruction manual appended to a chemical synthesizer, and a resulting product synthesized can be purified by a HPLC method using reverse phase chromatography and the like.

The polynucleotide encoding the protein of the present invention, and the antisense polynucleotides or portions thereof (a polynucleotide having a nucleotide sequence which comprises continuous 12 or more nucleotides) can be used as probes for screening the gene of the present invention from a cDNA library or the like. For said purpose, a polynucleotide with a GC content of 30 to 70% can preferably be used. A polynucleotide having a sequence comprising continuous 16 or more nucleotides may particularly preferred. Derivatives of the polynucleotides may be used as probes. In general, a sequence having nucleotides of the aforementioned number of nucleotides is recognized as a sequence with specificity.

As the cDNA libraries used for the screening with the above probe, those constructed from mRNA may preferably used. A class of cDNAs selected by random sampling from the above cDNA libraries may be used as a sample for the screening. Commercially available libraries may also be used. For example, DNA having a nucleotide sequence comprising a continuous 12 or more nucleotides of the nucleotide sequence set forth in SEQ ID NO: 2, 4 or 6 in the Sequence Listing, or a polynucleotide (antisense polynucleotide) that hybridizes to the DNA can be used as a probe for screening a DNA encoding any one of the amino acid sequences set forth in SEQ ID NOS: 1, 3 and 5 from the cDNA library or the like.

Moreover, a tissue in which an mRNA deriving from the gene of the present invention is expressed can be detected by means of Northern blotting hybridization for mRNAs deriving from various tissues using a polynucleotide encoding the protein of the present invention or an antisense polynucleotides thereof, or a fragment polynucleotide thereof as a probe.

Transformants can be prepared by inserting a cDNA capable of hybridizing to the gene of the present invention into an appropriate vector, and then introducing the recombinant vector into a host (for example, *Escherichia coli*). Types of the vectors and the hosts are not particularly limited, and an appropriate expression vector can be selected depending on the type of the host. As the host, any of bacteria such as *Escherichia coli*, yeast, or animal cells can be used. Animal cells are preferably used, and most preferably, mammal cells may be used. Methods for introducing the recombinant vector into an appropriate host such as *Escherichia coli* to obtain a transformant are not particularly limited. Any technique available to those skilled in the art can be employed.

The protein of the present invention can be produced by culturing the transformant, in which the gene of the present invention is introduced, to allow the cells to amplify the gene DNA or express the protein. A variety of literature and reports are available about the production and culture of transformants, and various techniques have been developed and widely used in the art. Accordingly, those skilled in the art can easily produce the protein of the present invention based on the nucleotide sequences set forth in the specification. As methods for introducing genes into cells, calcium chloride method, protoplast method, electroporation and the like may be used. Nuclear microinjection may be most preferably used.

Separation and purification of the target protein from a culture can be performed by the appropriate combination of techniques available to persons skilled in the art. For example, by performing procedures including concentration, solubilization, dialysis, and various types of chromatographies as required, the protein of the present invention can be efficiently recovered and purified. More specifically, the separation and purification may be carried out by appropriately choosing immunoprecipitation, salting out, ultrafiltration, isoelectric precipitation, gel filtration, electrophoresis, ion exchange chromatography, various affinity chromatography such as hydrophobic chromatography or antibody chromatography, chromatofocusing, adsorption chromatography, and reverse phase chromatography.

The protein of the present invention can be produced as a fusion peptide with other polypeptide(s). It should be understood that such fusion polypeptides also fall within the scope of the present invention. Types of the polypeptide to be fused are not particularly limited. An example includes a signal peptide which promotes extracellular secretion. The preparation of the fusion protein can also be preformed by using transformants. When the protein or the modified protein of the present invention is produced by using the fusion protein, the fusion protein is treated with a chemical substance such as cyanogen bromide or an enzyme such as a protease, and then the cleaved target product may be separated and purified.

A fusion protein may also be prepared which composes of a partial polypeptide responsible for epimorphin-like biological activities in the protein or modified protein of the present invention (so called an active domain) and other polypeptide. The above-mentioned domain 1 and/or domain 2 can be used as such active domains. For example, a soluble polypeptide containing an active domain can be produced by removing domain 4, and a fusion protein composed of the solubilized active domain and other polypeptide (e.g., a signal peptide) can be produced. A chimeric epimorphin may be produced by appropriately combining plural domains selected from each of the above domains of the protein of the present invention and each of the domains of the other types of epimorphin. Furthermore, a fusion protein may be produced by binding other polypeptide to a polypeptide composed of an appropriate combination of each of the above domains.

An antibody recognizing the protein of the present invention can be produced by using the protein of the present invention or a partial polypeptide chain thereof. The antibody of the present invention can be produced by sensitizing and immunizing a mammal with the protein of the present invention according to methods widely used in the art. Whether or not the antibody can recognize the protein of the present invention is determined by a method such as Western blotting, ELISA, or immunostaining (e.g., measurement by FACS). As immunogens, the protein of the present invention as well as a part of the protein bound to a carrier protein, e.g., bovine serum albumin may be used. The part of the protein of the present invention may preferably comprise eight or more amino acid residues, and such polypeptide may be synthesized, for example, by using a peptide synthesizer.

A monoclonal antibody generated by a hybridoma which is produced by using lymphocytes of an immunized animal may be used as the antibody of the present invention. Methods for preparing monoclonal antibodies are well known in the art and widely used (Antibodies A Laboratory Manual, a Cold Spring Harbor Laboratory Press, 1988, Chapter 6). In addition, active fragments of the above antibody can be used as the antibody of the present invention. In the specification, "active fragments" means fragments of an antibody having antigen-antibody reaction activity. More specifically, examples include $F(ab')_2$, Fab', Fab, and Fv. For example, where the antibody of the present invention is decomposed with pepsin, $F(ab')_2$ is obtained; where decomposed with papain, Fab is obtained. Where $F(ab')_2$ is reduced with a reagent such as 2-mercaptoethanol and then alkylated with monoiodoacetic acid, Fab' is obtained. Fv is a monovalent active antibody fragment composed of a heavy-chain variable region and a light-chain variable region bound with a linker to each other. A chimeric antibody can be obtained by preserving these active fragments and replacing the other part with fragments deriving from other animals. Any of the above described antibodies and active fragments and the like fall within the scope of the present invention.

The protein of the present invention can be detected by a method utilizing an antibody or an enzymatic reaction. Examples of the methods for detecting the protein of the present invention using an antibody include (I) a method for detecting the protein of the present invention using the aforementioned antibody with labeling, and (II) a method for detecting the protein of the present invention using the aforementioned antibody and a labeled secondary antibody recognizing said antibody. As means for labeling, radioactive isotopes (R1), enzymes, avidin or biotin, or fluorescent materials (FITC, rhodamine, and the like) may be utilized. Examples of methods utilizing an enzymatic reaction include ELISA, immunoagglutination, Western blotting, a process for identifying an immunoreactive molecule using flow cytometry and methods similar thereto.

EXAMPLES

The present invention will be explained more specifically by way of examples. However, the scope of the present invention is not limited to the following examples.

The sheep and bovine epimorphin genes of the present invention were obtained by the methods set out below.

1. Isolation of epimorphin cDNA

1) DNA to be used as a probe was labeled using Random Primed DNA Labeling Kit (manufactured by Boehringer Manheim) according to the instructions appended to the kit. DNA comprising the full length of a nucleotide sequence of a mouse epimorphin-coding region was used as a DNA probe.

2) DNA reaction solution having the following composition was then prepared. The solution was incubated for 30 minutes at 37° C., and then heated for 10 minutes at 65° C. for inactivation of enzymes.

| | |
|---|---|
| DNA probe (50 ng/μl) | 2 μl |
| $H_2O$ | 7 μl |
| dNTPs | 3 μl |
| [α-$^{32}$P]d-CTP (370MBq/ml) (manufactured by Amersham Pharmacia Biotech) | 5 μl |
| Primer | 2 μl |
| Klenow enzyme | 1 μl |
| Total | 20 μl |

3) The reaction solution was centrifuged with a Centri-Sep spin column (manufactured by Princeton Separations, Inc.) swollen with $H_2O$, thereby obtaining a labeled DNA probe.

4) Using the sheep lung and cow lung as libraries (Uni-ZAPXR Library, ST, manufactured by STRATAGENE), phage plaques were obtained by a standard method (New Cell Technology Experimental Protocol, Shu-jun sha).

5) The labeled DNA probe obtained in 3) were measured by using a scintilation counter, added to a hybridization reaction solution to 1×10$^6$ cpm/ml. Then, the product was allowed to react with a nylon membrane to which cDNA derived from the plaque was immobilized (Hybond-N+, manufactured by Amersham Pharmacia Biotech).

Prehybridization

Reaction solution: ExpressHyb (manufactured by Clontech Laboratoreis, Inc.)

Reaction temperature: 68° C.

Reaction time: 30 minutes

Hybridization

Reaction solution: ExpressHyb (manufactured by Clontech Laboratories, Inc.)

$^{32}$p labeled cDNA probe: 1×10$^6$ cpm/ml

Reaction temperature: 68° C.

Reaction time: 1 hour

6) The membrane after the hybridization was washed with the solution as described below according to the protocols for ExpressHyb (manufactured by Clontech Laboratories, Inc.)

2×SSC, 0.05% SDS 500 ml

Room temperature

Time: 40 minutes 0.1×SSC, 0.1% SDS

50° C.

Time: 40 minutes

7) The washed nylon membrane was exposed to X-ray film (e.g., XAR 5 film manufactured by Eastman Kodak Company) overnight at −80° C. to take autoradiographs.

8) Positions of positive plaques were determined based on the resulting autoradiographs, and then phages in the corresponding plaques on the agar were recovered in an SM solution.

9) The recovered phages were again allowed to form plaques on a NZY agar medium by a standard method, and then immobilized on a nylon membrane.

10) Procedures 5) to 9) were repeated 3 times to obtain unified phages in positive plaques. The phages were collected and suspended in 500 μl of SM solution. The suspension was added with 20 μl of chloroform and stirred to prepare a phage solution. cDNA isolated from the phage solution contained sheep and bovine epimorphin genes.

2. Preparation of sheep and bovine epimorphin cDNA in large quantity 1) 10 μl of the phage solution suspended in the SM solution, 200 μl of XL1-Blue *Escherichia coli* (manufactured by STRATAGENE), and 1 μl of helper phages (manufactured by STRATAGENE) were mixed and allowed to react for 15 minutes at 37° C.

2) The mixed solution was then transferred in 3 ml of LB medium, and the medium was shake-cultured overnight at 37° C. to cleave and recover the genes as pBluescript phagemid.

3) The phagemid was treated for 20 minutes at 70° C. and centrifuged at 1000 rpm for 15 minutes, and then the supernatant was recovered.

4) 100 μl of the supernatant and 200 μl of SOLR *Eseherichia coli* were mixed, and then the mixture was allowed to react for 15 minutes at 37° C.

5) 10 μl of the solution obtained in 4) was inoculated over a plate of LB medium containing 50 μg/ml of ampicillin, and then the plate was cultured overnight at 37° C.

6) One colony was added to 3 ml of an LB medium containing 50 μg/ml of ampicillin, and then the medium was shake-cultured overnight at 37° C.

7) The culture product was centrifuged at 2000 rpm for 10 minutes to recover the *E. coli.*

8) The *E. coli* was purified using a Plasmid Mini Kit (manufactured by QIAGEN) to prepare plasmid DNA containing sheep or bovine epimorphin genes in a large quantity.

3. Sequencing of sheep and bovine epimorphin cDNA The entire nucleotide sequences of sheep and bovine epimorphin genes in the plasmid DNA were determined by the dye terminator method using an auto sequencer.

4. Determination of amino acid sequences

Amino acid sequences of sheep and bovine epimorphin were determined based on the nucleotide sequences determined in the above step 3 (Genetics-Mac provided by Software Development Co., Ltd. was used as a computer software for this step).

Each of the amino acid sequences was named; sheep epimorphin 2, bovine epimorphin 2, and bovine epimorphin 4.

5. Preparation of transformants cDNA of each of sheep epimorphin 2, bovine epimorphin 2, and bovine epimorphin 4 was inserted into pBluescript SK(−) plasmid, and then the plasmid was introduced in *Escherichia coli* strain SOLR to obtain transformants. The resulting respective transformants were named as Sh-EPM2, Bo-EPM2, and Bo-EPM4.

INDUSTRIAL APPLICABILITY

The protein of the present invention can exert epimorphin-like biological nactivities including, for example, differentiation of milk protein-producing cells into branched luminal structure, and promotion of hair growth. The protein of the present invention can be used as a medicament for Artiodactyls or as an agent for modifying animal properties. For example, the protein of the present invention enlarges the mammary glands of Artiodactyls including cows and sheep to prevent the gland from clogging, thereby an yield of a desired protein secreted in the milk of the animal is increased. Furthermore, sheep for a high productivity of wool and transgenic animals (an animal factory) for a high productivity of a target protein can be generated by using the gene of the present invention.

What is claimed is:

1. An isolated protein comprising any one of the amino acid sequences set forth in SEQ ID NOS: 1, 3, and 5 in the Sequence Listing.

2. An isolated protein having 98% or more homology to an amino acid sequence from the 1st to 262nd amino acids of the amino acid sequence set forth in SEQ ID NO: 1 in the Sequence Listing, and which has an activity of enlarging mammary glands.

3. The protein according to claim 2 having an amino acid sequence from the 1st to 262nd amino acids of the amino acid sequence set forth in SEQ ID NO: 1 in the Sequence Listing.

4. The protein according to claim 2 having an amino acid sequence from the 1st to 262nd amino acids of the amino acid sequence set forth in SEQ ID NO: 5 in the Sequence Listing.

5. An isolated protein having any one of the amino acid sequences set forth in SEQ ID NOS: 1, 3 and 5 in the Sequence Listing wherein one or more amino acids is substituted, which has 98% or more homology to the amino acid sequence disclosed in SEQ ID NOS: 1, 3 or 5 and which induces differentiation of a milk protein-producing cell into a branched luminal structure.

6. An isolated protein in which one or more amino acids is substituted in an amino acid sequence defined by the 1st to 262nd amino acids of either of the amino acid sequence set forth in SEQ ID NOS: 1 or 5 in the Sequence Listing, which has 98% or more homology to the amino acid sequence defined by the 1st to 262nd amino acids of either of the amino acid sequence set forth in SEQ ID NO: 1 or 5 and induces differentiation of a milk protein-producing cell into a branched luminal structure.

7. An isolated protein having any one of the amino acid sequences set forth in SEQ ID NOS: 1, 3, and 5 in the Sequence Listing wherein one or more amino acids is substituted which has 98% or more homology to the amino acid sequence disclosed in SEQ ID NOS: 1, 3 or 5 and which promotes hair growth.

8. An isolated protein in which one or more amino acids is substituted in an amino acid sequence defined by the 1st to 262nd amino acids of either of the amino acid sequences set forth in SEQ ID NOS: 1 or 5 in the Sequence Listing, which has 98% or more homology to the amino acid sequence defined by the 1st to 262nd amino acids of either of the amino acid sequences set forth in SEQ ID NO: 1 or 5 and promotes hair growth.

9. An isolated polynucleotide encoding the protein according to claim 1.

10. An isolated polynucleotide according to claim 9, which is a DNA set forth in SEQ ID NO: 2, 4 or 6.

11. An isolated protein having 98% or more homology to an amino acid sequence form the 1st to 262nd amino acids of the amino acid sequence set forth in SEQ ID NO:1in the Sequence Listing, and which promotes hair growth.

* * * * *

UNITED STATES PATENT AND TRADEMARK OFFICE

CERTIFICATE OF CORRECTION

PATENT NO. : 6,838,548 B1
DATED : January 4, 2005
INVENTOR(S) : K. Tsuganezawa

It is certified that error appears in the above-identified patent and that said Letters Patent is hereby corrected as shown below:

Column 20,
Line 11, "form" should be -- from --.

Signed and Sealed this

Sixteenth Day of August, 2005

JON W. DUDAS
*Director of the United States Patent and Trademark Office*

SEQUENCE LISTING

<160> NUMBER OF SEQ ID NOS: 6

<210> SEQ ID NO 1
<211> LENGTH: 287
<212> TYPE: PRT
<213> ORGANISM: Bovine

<400> SEQUENCE: 1

```
Met Arg Asp Arg Leu Pro Asp Leu Thr Ala Cys Arg Lys Asn Asp Asp
1               5                   10                  15

Gly Asp Thr Thr Val Val Val Glu Lys Asp His Phe Met Asp Asp Phe
            20                  25                  30

Phe His Gln Val Glu Glu Ile Arg Asn Ser Ile Ala Lys Ile Ala Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Thr Lys Leu Lys Ser Ile Glu
                85                  90                  95

Gln Ser Phe Asp Gln Asp Glu Gly Gly Asn Arg Thr Ser Val Glu Leu
            100                 105                 110

Arg Ile Arg Arg Thr Gln His Ser Val Leu Ser Arg Lys Phe Val Glu
        115                 120                 125

Val Met Thr Glu Tyr Asn Glu Ala Gln Thr Leu Phe Arg Glu Arg Ser
    130                 135                 140

Lys Gly Arg Ile Gln Arg Gln Leu Glu Ile Thr Gly Lys Thr Thr Thr
145                 150                 155                 160

Asp Asp Glu Leu Glu Glu Met Leu Glu Ser Gly Asn Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Lys Asn Val Met Asn Ala Ala
225                 230                 235                 240

Asp Tyr Val Glu His Ala Lys Glu Glu Thr Lys Lys Ala Ile Lys Tyr
                245                 250                 255

Gln Ser Lys Ala Arg Arg Lys Met Met Phe Ile Ile Ile Cys Val Val
            260                 265                 270

Ile Leu Leu Val Ile Leu Gly Ile Ile Leu Ala Thr Thr Leu Ser
        275                 280                 285
```

<210> SEQ ID NO 2
<211> LENGTH: 864
<212> TYPE: DNA
<213> ORGANISM: Bovine

<400> SEQUENCE: 2

```
atgcgggacc ggctgccgga cctgacggcg tgtaggaaaa atgatgatgg ggacacaact     60

gttgttgttg aaaaggacca ttttatggat gatttcttcc atcaggtcga ggagatcaga    120

aacagtatag cgaaaatagc tcagtatgtc gaagaagtga agaaaaacca cagcatcatt    180
```

```
ctttctgcac caaacccaga aggaaaaata aaggaagagc ttgaagatct gaacaaagaa    240

atcaagaaaa ctgctaataa aataaggact aagttgaagt ctattgaaca gagttttgat    300

caggatgagg gtggaaaccg aacttctgtg gagcttcgga tacgaagaac ccagcattca    360

gtgctatctc gaaagtttgt ggaagtcatg acagaatata acgaagcaca gactctgttt    420

cgggagcgaa gcaaaggccg tatacagcgt cagctagaaa taactggaaa aactaccacc    480

gatgatgagc tggaagagat gctggaaagt gggaatccct ccatcttcac gtcagatatt    540

atatcagatt cacaaattac tagacaggct ctcaatgaaa ttgagtcccg tcataaagac    600

atcatgaagc tggagacaag catccgtgag ctacatgaga tgttcatgga catggccatg    660

ttcgtcgaga ctcagggtga aatgatcaac aacatagaaa aaaatgttat gaatgccgca    720

gactatgtag aacatgcaaa agaagaaacg aagaaagcta ttaaatatca aagcaaagca    780

agaaggaaaa tgatgttcat tattatttgt gtagttattt tgcttgtgat ccttggaatt    840

atcctagcaa caacattgtc atag                                           864
```

```
<210> SEQ ID NO 3
<211> LENGTH: 269
<212> TYPE: PRT
<213> ORGANISM: Bovine

<400> SEQUENCE: 3

Met Arg Asp Arg Leu Pro Asp Leu Thr Ala Cys Arg Lys Asn Asp Asp
1               5                   10                  15

Gly Asp Thr Thr Val Val Val Glu Lys Asp His Phe Met Asp Asp Phe
            20                  25                  30

Phe His Gln Val Glu Glu Ile Arg Asn Ser Ile Ala Lys Ile Ala Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Thr Lys Leu Lys Ser Ile Glu
                85                  90                  95

Gln Ser Phe Asp Gln Asp Glu Gly Gly Asn Arg Thr Ser Val Glu Leu
            100                 105                 110

Arg Ile Arg Arg Thr Gln His Ser Val Leu Ser Arg Lys Phe Val Glu
        115                 120                 125

Val Met Thr Glu Tyr Asn Glu Ala Gln Thr Leu Phe Arg Glu Arg Ser
    130                 135                 140

Lys Gly Arg Ile Gln Arg Gln Leu Glu Ile Thr Gly Lys Thr Thr Thr
145                 150                 155                 160

Asp Asp Glu Leu Glu Glu Met Leu Glu Ser Gly Asn Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Lys Asn Val Met Asn Ala Ala
225                 230                 235                 240

Asp Tyr Val Glu His Ala Lys Glu Glu Thr Lys Lys Ala Ile Lys Tyr
```

```
            245                 250                 255

Gln Ser Lys Ala Arg Arg Val Ser Leu Val Phe Gln Ser
            260                 265


<210> SEQ ID NO 4
<211> LENGTH: 810
<212> TYPE: DNA
<213> ORGANISM: Bovine

<400> SEQUENCE: 4

atgcgggacc ggctgccgga cctgacggcg tgtaggaaaa atgatgatgg ggacacaact      60

gttgttgttg aaaaggacca ttttatggat gatttcttcc atcaggtcga ggagatcaga     120

aacagtatag cgaaaatagc tcagtatgtc gaagaagtga agaaaaacca cagcatcatt     180

ctttctgcac caaacccaga aggaaaaata aaggaagagc ttgaagatct gaacaaagaa     240

atcaagaaaa ctgctaataa aataaggact aagttgaagt ctattgaaca gagttttgat     300

caggatgagg gtggaaaccg aacttctgtg gagcttcgga tacgaagaac ccagcattca     360

gtgctatctc gaaagtttgt ggaagtcatg acagaatata acgaagcaca gactctgttt     420

cgggagcgaa gcaaaggccg tatacagcgt cagctagaaa taactggaaa aactaccacc     480

gatgatgagc tggaagagat gctggaaagt gggaatccct ccatcttcac gtcagatatt     540

atatcagatt cacaaattac tagacaggct ctcaatgaaa ttgagtcccg tcataaagac     600

atcatgaagc tggagacaag catccgtgag ctacatgaga tgttcatgga catggccatg     660

ttcgtcgaga ctcagggtga aatgatcaac aacatagaaa aaaatgttat gaatgccgca     720

gactatgtag aacatgcaaa agaagaaacg aagaaagcta ttaaatatca aagcaaagca     780

agaaagggtga gtttggtctt tcagagttga                                      810


<210> SEQ ID NO 5
<211> LENGTH: 287
<212> TYPE: PRT
<213> ORGANISM: ovis

<400> SEQUENCE: 5

Met Arg Asp Arg Leu Pro Asp Leu Thr Ala Cys Arg Lys Asn Asp Asp
1               5                   10                  15

Gly Asp Thr Thr Val Val Val Glu Lys Asp His Phe Met Asp Asp Phe
            20                  25                  30

Phe His Gln Val Glu Glu Ile Arg Asn Ser Ile Ala Lys Ile Ala Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Thr Lys Leu Lys Ser Ile Glu
                85                  90                  95

Gln Ser Phe Asp Gln Asp Glu Gly Gly Asn Arg Thr Ser Val Glu Leu
            100                 105                 110

Arg Ile Arg Arg Thr Gln His Ser Val Leu Ser Arg Lys Phe Val Glu
        115                 120                 125

Val Met Thr Glu Phe Asn Glu Ala Gln Thr Leu Phe Arg Glu Arg Ser
    130                 135                 140

Lys Gly Arg Ile Gln Arg Gln Leu Glu Ile Thr Gly Lys Thr Thr Thr
145                 150                 155                 160
```

-continued

```
Asp Asp Glu Leu Glu Glu Met Leu Glu Ser Gly Asn Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Lys Asn Val Thr Asn Ala Ala
225                 230                 235                 240

Asp Tyr Val Glu His Ala Lys Glu Glu Thr Lys Lys Ala Ile Lys Tyr
                245                 250                 255

Gln Ser Lys Ala Arg Arg Lys Met Met Phe Ile Ile Ile Cys Val Val
            260                 265                 270

Ile Leu Leu Val Ile Phe Gly Ile Ile Leu Ala Thr Thr Leu Ser
        275                 280                 285


<210> SEQ ID NO 6
<211> LENGTH: 864
<212> TYPE: DNA
<213> ORGANISM: ovis

<400> SEQUENCE: 6

atgcgggacc ggctgccgga cctgacggcg tgtaggaaaa atgatgatgg ggacacaact     60

gttgttgttg aaaaggacca ttttatggat gatttcttcc atcaggtcga ggagatcaga    120

aacagtatag caaaaatagc tcagtatgtc gaagaagtga agaaaaacca cagcatcatt    180

ctttctgcac caaacccaga aggaaaaata aaggaagagc ttgaagatct gaacaaagaa    240

atcaagaaaa ctgccaataa aattcggact aagttgaagt ctattgaaca gagttttgat    300

caggatgagg gtggaaaccg aacttctgtg gagcttcgga tacgaagaac ccagcattca    360

gtgctatctc gaaagtttgt ggaagtcatg acagaattta atgaagcaca gactctgttt    420

cgggagcgaa gcaaaggccg tatacagcgt cagctagaaa taactggaaa aactaccacc    480

gatgatgagc tggaagagat gctggaaagt gggaatccct ccatcttcac gtcagatatt    540

atatcagatt cacaaatcac tagacaggct ctgaatgaaa ttgagtcccg tcataaagac    600

atcatgaagc tggagacgag catccgtgag ctgcacgaga tgttcatgga catggccatg    660

ttcgtcgaga cccagggtga aatgatcaac aacatagaaa aaaatgttac gaatgccgca    720

gactatgttg agcatgctaa agaagaaacg aagaaagcca ttaaatatca aagcaaagca    780

agaaggaaaa tgatgttcat tattatctgt gtagttattt tgcttgtgat ctttggaatt    840

atcctagcaa caacattgtc atag                                           864
```